United States Patent [19]

Okada

[11] Patent Number: 4,691,705
[45] Date of Patent: Sep. 8, 1987

[54] CALCULUS CRUSHING APPARATUS

[75] Inventor: Tsutomu Okada, Tokyo, Japan

[73] Assignee: Olympus Optical Co., Ltd., Tokyo, Japan

[21] Appl. No.: 822,019

[22] Filed: Jan. 24, 1986

[30] Foreign Application Priority Data

Feb. 8, 1985 [JP] Japan ................................. 60-22962

[51] Int. Cl.[4] ............................................ A61B 17/22
[52] U.S. Cl. ..................................... 128/328; 128/320
[58] Field of Search ............................ 128/320, 328, 7

[56] References Cited

U.S. PATENT DOCUMENTS

| | | | |
|---|---|---|---|
| 4,046,149 | 9/1977 | Komiya | 128/328 |
| 4,198,960 | 4/1980 | Utsugi | 128/328 |
| 4,203,429 | 5/1980 | Vasilevsky et al. | 128/328 |
| 4,243,040 | 1/1981 | Beecher | 128/328 |
| 4,590,938 | 5/1986 | Segura et al. | 128/328 |
| 4,611,594 | 9/1986 | Grayhack | 128/328 |

FOREIGN PATENT DOCUMENTS

3206846 4/1984 Fed. Rep. of Germany .
2604024 8/1986 Fed. Rep. of Germany .

Primary Examiner—Albert J. Makay
Assistant Examiner—David W. Westphal
Attorney, Agent, or Firm—Frishauf, Holtz, Goodman & Woodward

[57] ABSTRACT

A calculus crushing apparatus includes a flexible sheath to be inserted into the body cavity. An operating wire is slidably inserted into the sheath, and a basket for seizing and crushing the calculus is coupled to the distal end of the wire. The sheath has a first sheath having a predetermined strength and a second sheath which is weaker but more flexible than the first sheath. The first sheath is movably inserted into the second sheath. The flexible sheath is inserted into the body cavity while the second sheath projects sufficiently beyond the distal end of the first sheath. After the first sheath is moved to a position where the distal end of the first sheath extends beyond that of the second sheath, the operation wire is pulled to retract the basket, thereby crushing the calculus seized by the basket.

8 Claims, 12 Drawing Figures

CALCULUS CRUSHING APPARATUS

BACKGROUND OF THE INVENTION

The present invention relates to a calculus crushing apparatus for crushing a calculus produced in the body cavity.

Calculi produced in the bile duct, bladder and other internal organs adversely influence the human body, and hypertrophied calculi are extremely painful.

Thereupon, calculus crushing apparatuses have conventionally been developed which are inserted into the body cavity through an endoscope. These apparatuses are used to crush or completely remove a calculus in the body cavity from the cavity. According to one such prior art crushing apparatus, a catch basket formed of resilient wires is fixed to the distal end of an operating wire, and the operating wire, along with the basket, is inserted into a flexible sheath having a rigid portion at its distal end. The basket is spread or folded by advancing or retreating the operating wire at the rear end of the sheath. After seizing the calculus by means of the basket projecting from the distal end of the sheath, the operating wire is pulled to draw the basket into the sheath. Thus, the basket is folded to break the calculus therein into small pieces.

In the crushing apparatus of this type, the flexible sheath is formed of a close coil or other suitable material which is strong enough to stand a force applied thereto during a calculus crushing operation. The close coil, however, is extremely stable and exhibits strong resistance to bending. Therefore, the sheath cannot easily be inserted into curved regions of a body cavity, e.g., into the bile duct via the duodenal papilla, and may possibly injure or puncture the body wall during the insertion.

Such a situation may be eliminated by using a sufficiently flexible material for the flexible sheath. In this case, however, the sheath would not be strong enough to resist the force exerted thereon during the crushing operation, and thus fail to reliably crush the calculus.

SUMMARY OF THE INVENTION

The present invention is contrived in consideration of these circumstances, and is intended to provide a calculus crushing apparatus capable of being inserted into curved portions of a body cavity without injuring the body wall as well as reliably crushing calculi.

In order to achieve the above object, according to a crushing apparatus of the present invention, a flexible sheath includes a first sheath having a predetermined strength and a second sheath which is weaker but more flexible than the first sheath. The first and second sheaths can be moved relatively between a position where the first sheath extends beyond the distal end of the second sheath, and a position where the second sheath projects sufficiently beyond the distal end of the first sheath. In inserting the flexible sheath into the body cavity, the second sheath, which is more flexible, is extended beyond the distal end of the first one. In crushing a calculus after the insertion, the first sheath is extended farther.

BRIEF DESCRIPTION OF THE DRAWINGS

FIGS. 1 to 7 show a calculus crushing apparatus according to a first embodiment of the present invention, in which

FIGS. 9 to 11 show a third embodiment of the invention, in which

DETAILED DESCRIPTION OF THE PREFERRED EMBODIMENTS

Embodiments of the present invention will now be described in detail with reference to the accompanying drawings.

Figure 1:
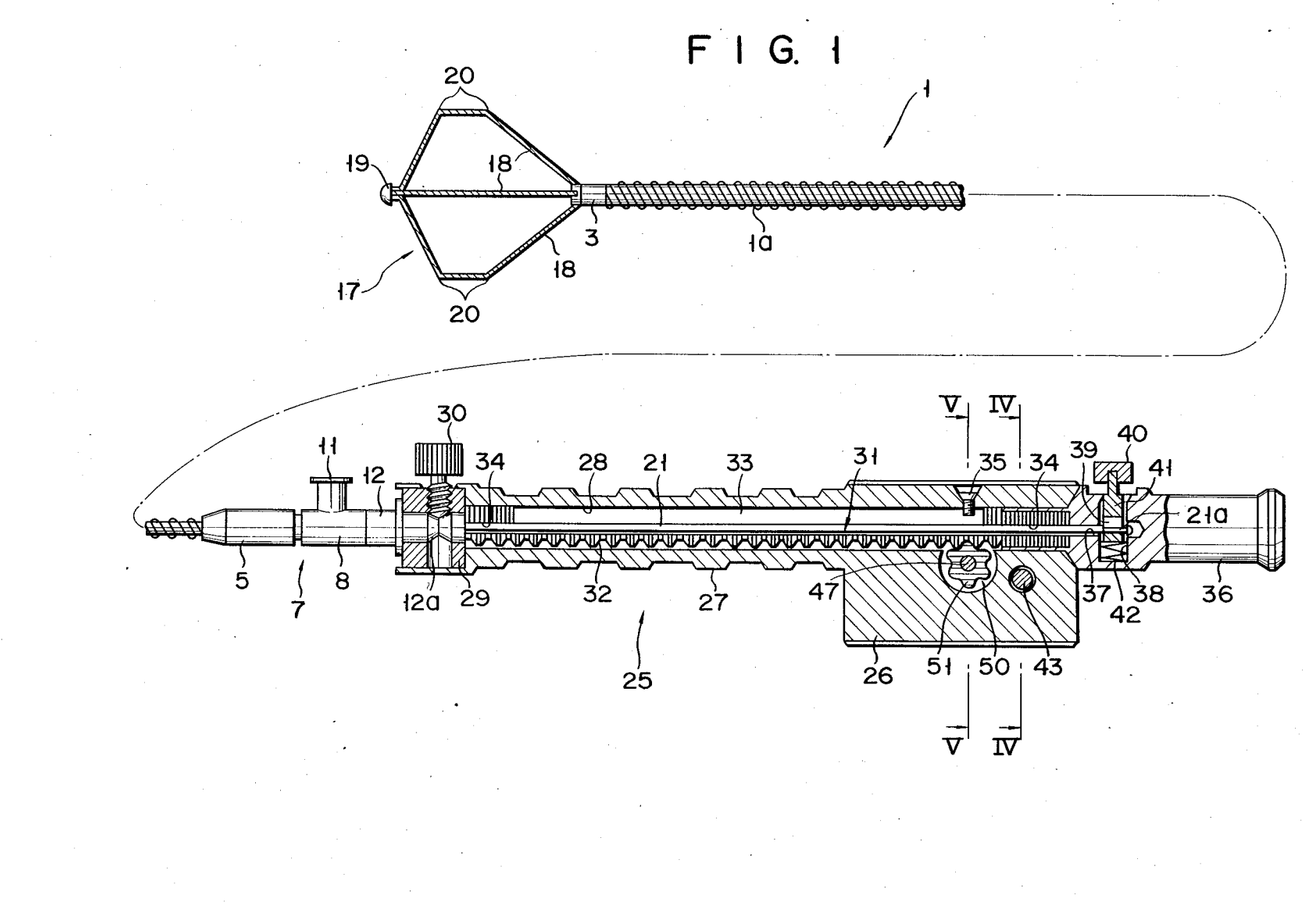
FIG. 1 is a cutaway, general side view of the apparatus.

Generally, a calculus crushing apparatus comprises elongate flexible sheath 1 adapted to be inserted into the body cavity and mouthpiece 7 attached to the proximal end of sheath 1, as shown in FIG. 1. An operating wire, as described in detail later, is inserted in sheath 1. Basket 17 for seizing a foreign object is coupled to the distal end of the wire, projecting from the distal end of sheath 1. Mouthpiece 7 is connected to operating section 25 for pushing and pulling the wire.

Figure 2:
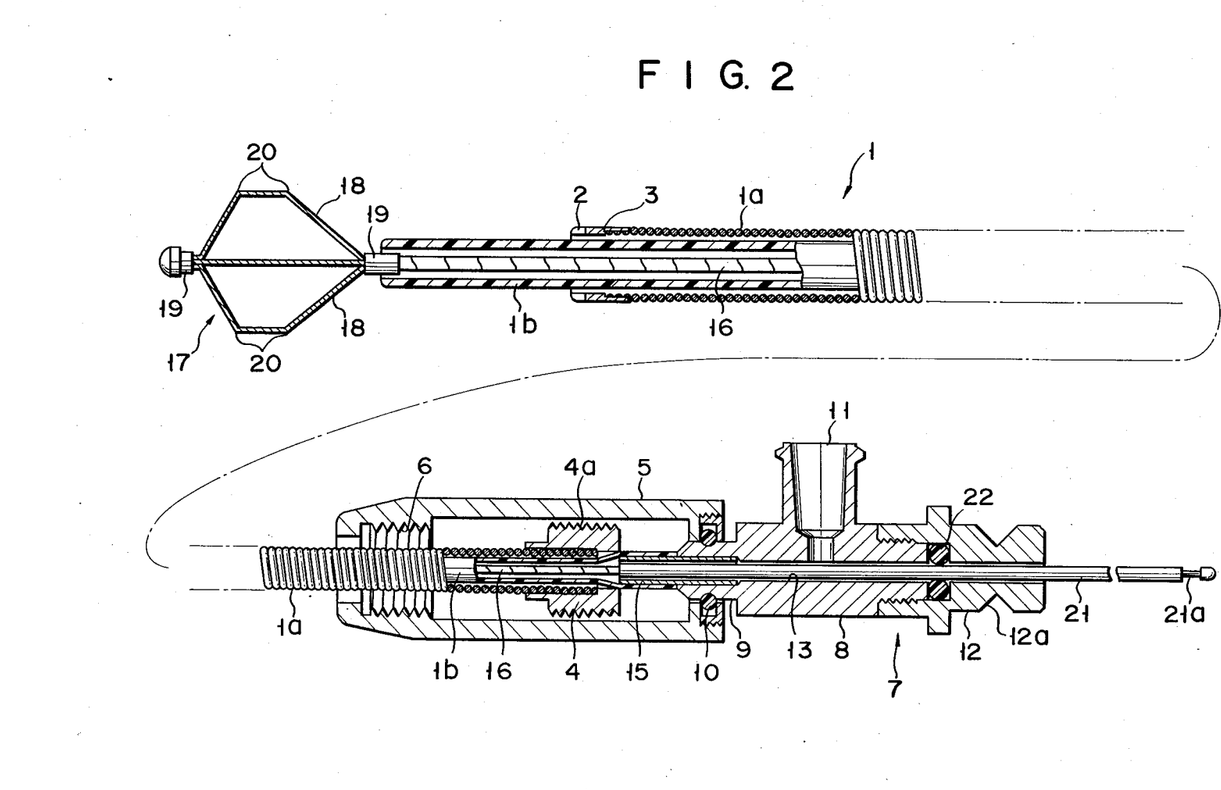
FIG. 2 is a sectional view showing a flexible sheath and a mouthpiece.

As shown in FIG. 2, sheath 1 is of dual structure, including first sheath 1a and second sheath 1b inserted in the first one. Sheaths 1a and 1b are movable relative to the other. Sheath 1a is formed of a close coil which is strong enough to stand a force applied thereto during calculus crushing operation. Cylindrical rigid member 3 with wire escape cut 2 is fixed to the distal end of sheath 1a, while cylindrical retaining member 4 is fixed around the proximal end portion of sheath 1a. External threaded portion 4a is formed on the outer peripheral surface of member 4. Member 4 is movably housed in holding cylinder 5 which is arranged around the proximal end portion of sheath 1a. Internal threaded portion 6 to engage threaded portion 4a of member 4 is formed on the inner surface of the front end of cylinder 5. Cylinder 5 is rotatably mounted on mouthpiece 7. Mouthpiece 7 includes first and second members 8 and 12 engaging each other. Boss portion 9 protrudes forward from first member 8. The rear end of holding cylinder 5 is rotatably supported, in a liquid-tight manner, on the outer peripheral surface of portion 9 through O-ring 10. Mouthpiece 7 has through hole 13 extending through first and second members 8 and 12 and boss portion 9, and liquid feed port 11 communicating with hole 13.

Figure 3:
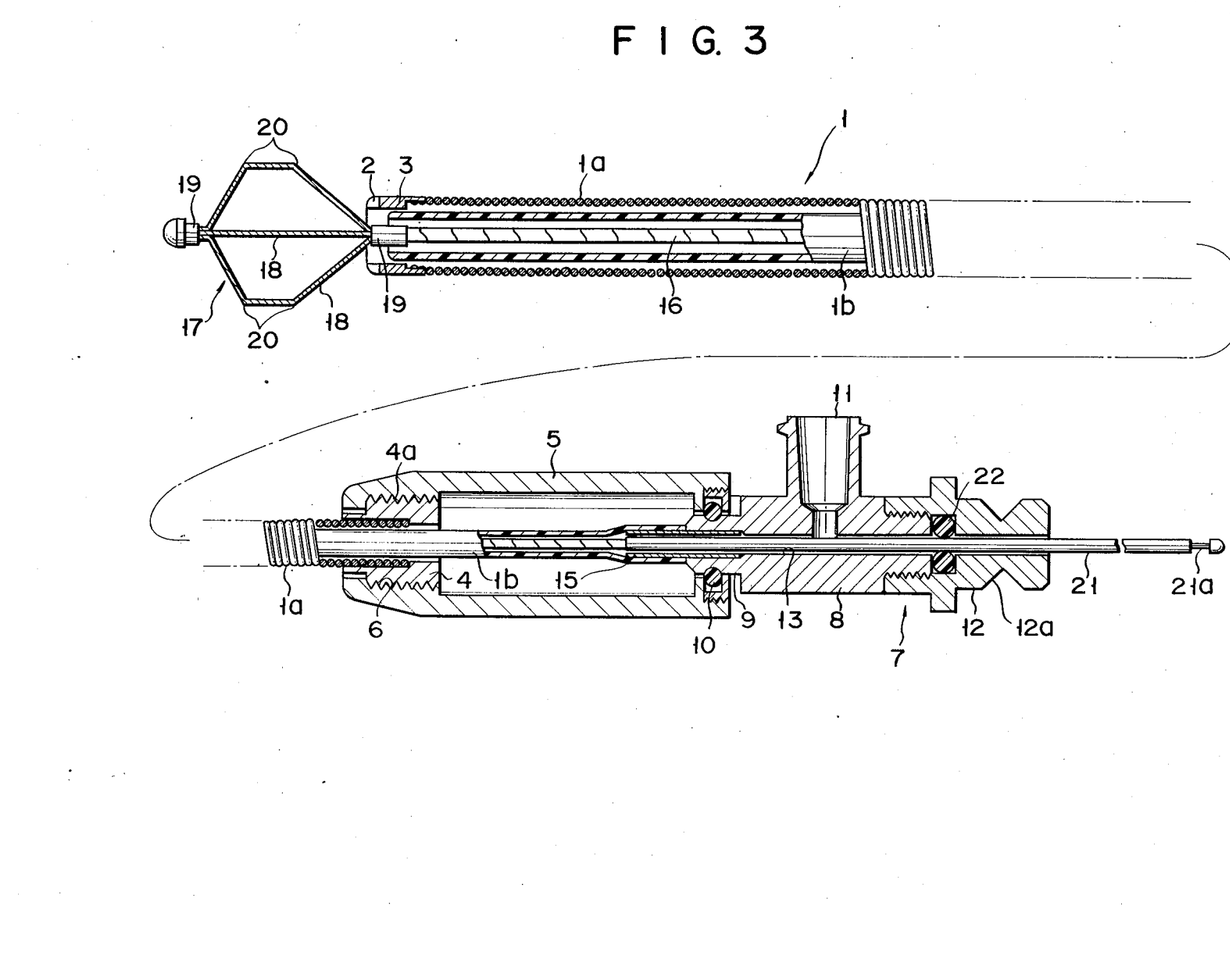
FIG. 3 is a sectional view similar to FIG. 2, showing an operating state different from the one shown in FIG. 2.

First sheath 1a is penetrated by second sheath 1b which is weaker but more flexible than sheath 1a. Sheath 1b is formed of a flexible resin, such as fluorine-contained polymer, Teflon, etc. One end of connecting pipe 15 is fixedly inserted in through hole 13 of boss portion 9 of mouthpiece 7 so that pipe 15 projects forward from portion 9. The proximal end portion of sheath 1b is fitted on the projecting end portion of pipe 15 in a liquid-tight manner. Thus, first sheath 1a is slidably mounted on second sheath 1b. When sheath 1a is slid forward so that retaining member 4 fixed on the proximal end of sheath 1a is screwed in threaded portion 6 of holding cylinder 5, sheath 1a is held in a position where its distal end extends beyond that of sheath 1b, as shown in FIG. 3.

As shown in FIG. 2, operating wire 16 is slidably passed through second sheath 1b. Basket 17 for seizing and crushing a calculus or other foreign object is coupled to the distal end of wire 16. Basket 17 is formed by coupling a plurality of resilient wires 18 to one another at both the front and rear ends thereof by means of front and rear tips 19, respectively. Bent portions 20 is formed in the middle of each wire 18. Thus, basket 17 can extend and contract or is collapsible in the axial direction of operating wire 16. The distal end of straight, elongate coupling rod 21 is fixed to the proximal end of wire 16. Rod 21 is slidably passed through hole 13 of mouthpiece 7, extending rearward from the mouthpiece. O-ring 22 is disposed at the junction between first and second members 8 and 12 of mouthpiece 7, whereby through hole 13 is kept liquid-tight. Rod 21 penetrates ring 22. A liquid, such as a contrast medium, can be fed into second sheath 1b through liquid feed port 11.

Operating section 25 for operating the operating wire is removably connected to mouthpiece 7. As shown in FIG. 1, section 25 includes body 26 and grip portion 27 extending therefrom for an operator's grip. Insertion hole 28 is bored through body 26 and portion 27 in the extending direction of portion 27. Connecting ring 29 is attached to the distal end of grip portion 27 so as to be coaxial with hole 28. Setscrew 30 is screwed into ring 29 so as to be movable in the diametrical direction of ring 29. Mouthpiece 7 is connected to operating section 25 by inserting the rear end portion of second member 12 of mouthpiece 7 into ring 29, and screwing setscrew 30 into ring 29 so that the tip end of screw 30 engages groove 12a formed around the rear end portion of member 12. If mouthpiece 7 is connected to section 25, then coupling rod 21 is inserted in insertion hole 28.

Figure 4:
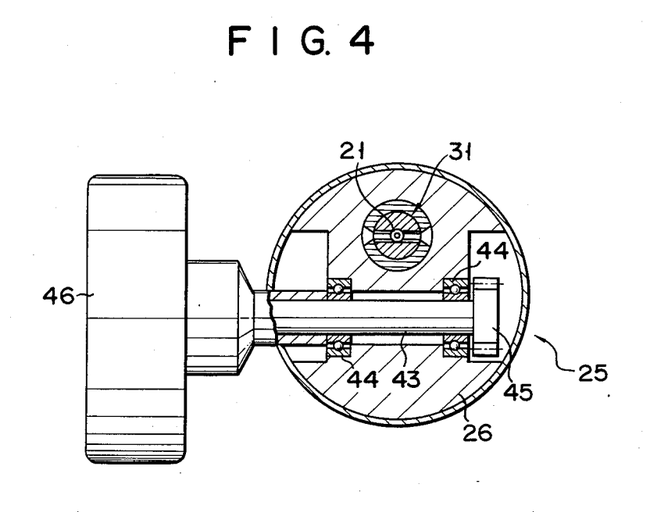
FIG. 4 is a sectional view taken along line IV—IV of FIG. 1.
Figure 5:
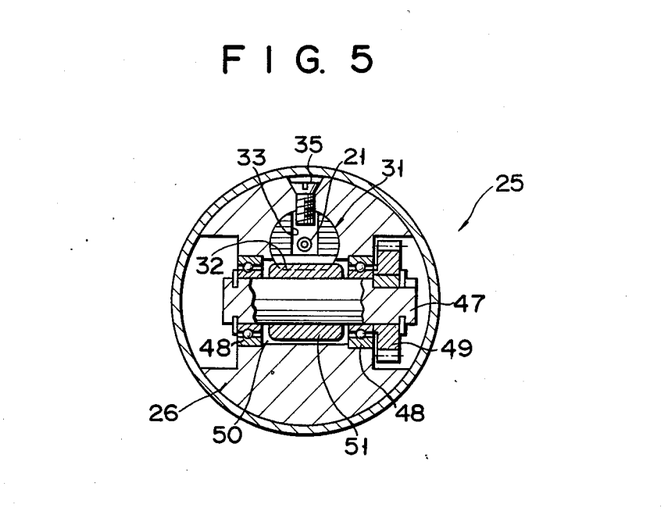
FIG. 5 is a sectional view taken along line V—V of FIG. 1.

As shown in FIGS. 1, 4 and 5, elongate rack structure 31 is slidably inserted in insertion hole 28 of operating section 25. Structure 31 has a circular cross section, and rack 32 is formed on one side of structure 31 throughout the axial length thereof. Guide groove 33 is formed in the whole region of structure 31 except both end portions thereof, opening on the opposite side of structure 31 to rack 32 and extending along the axis of the structure. Through hole 34 is formed coaxially in each end portion of rack structure 31, communicating with groove 33. Coupling rod 21 protrudes from the proximal end of structure 31, extending through holes 34 and groove 33. Guide screw 35 screwed in body 26 of operating section 25 is fitted in groove 33, whereby structure 31 is prevented from rotating in hole 28.

Handle portion 36 is coupled to the proximal end of rack structure 31, protruding rearward from operating section 25. Fitting hole 37 is formed in portion 36 so as to be coaxial with through hole 34 of structure 31. It communicates with guide groove 33 by means of hole 34. An extreme end of coupling rod 21 with flat portion 21a thereon is inserted in hole 37. Handle portion 36 is formed with receptacle hole 38 which extends at right angles to hole 37 and opens to the outer peripheral surface of portion 36. Retaining rod 41 with button 40 fixed on its top end is inserted in hole 38. Engaging hole 39 is bored through the middle portion of rod 41. Rod 41 is urged to project from portion 36 by spring 42 which is housed in receptacle hole 38. In connecting coupling rod 21 to handle portion 36, retaining rod 41 is first pushed in against the urging force of spring 42 so that holes 37 and 39 are aligned with each other, and, in this state, the extreme end of rod 21 is then inserted into fitting hole 37 to locate flat portion 21a in engaging hole 39. If the pressure on rod 41 is removed thereafter, portion 21a of rod 21 and hole 39 engage each other, so that rod 21 is connected to portion 36. Thus, operating wire 16 can be moved by pushing and pulling handle portion 36.

First support shaft 43 is rotatably supported in body 26 of operating section 25 by means of bearings 44, extending at right angles to rack structure 31. First gear 45 is fixed on one end of shaft 45, while knob 46 is mounted on the other end outside body 26. Moreover, second support shaft 47 is rotatably supported in body 26 by means of bearings 48, extending parallel to shaft 43. Shaft 47 is fixedly fitted, at one end thereof, with second gear 49 which engages first gear 45. There are more teeth on the second gear than on the first one. Cavity 50 is formed in body 26, opening into insertion hole 28. Shaft 47 extends through cavity 50. Cavity 50 contains third gear 51 which is fixed on shaft 47 and meshed with rack 32. If knob 46 is rotated, therefore, the rotation is decelerated by first and second gears 45 and 49 and transmitted to third gear 51. Then, gear 51 causes rack structure 31 to slide, thus moving operating wire 16 through the medium of coupling rod 21.

The operation of the crushing apparatus constructed in this manner will now be described.

Figure 6:
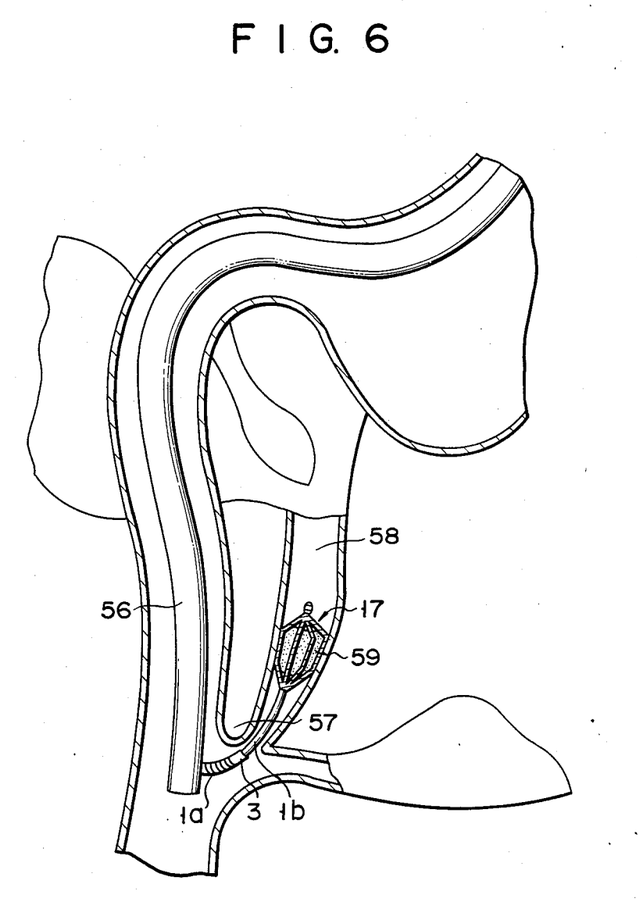
FIG. 6 is a schematic view showing a situation in which the sheath in the state of FIG. 2 is inserted in the body cavity.

First, operating section 25 is disengaged from mouthpiece 7, and retaining member 4 is removed from threaded portion 6 of holding cylinder 5 to retreat first sheath 1a, as shown in FIG. 2. As a result, second sheath 1b projects sufficiently beyond the distal end of first sheath 1a. Meanwhile, basket 17 is drawn into sheath 1b. In this state, flexible sheath 1 is inserted into a forceps channel (not shown) of the endoscope, and the endoscope, along with sheath 1 therein, is introduced into the body cavity. Subsequently, flexible sheath 1 is projected from the distal end of insertion section 56 of the endoscope, as shown in FIG. 6, and the distal end portion of sheath 1b is inserted into, for example, bile duct 58 through duodenal papilla 57. Formed of flexible material, sheath 1b can be bent easily and produces only a small reaction force when bent. Therefore, it will not injure duodenal papilla 57 or bile duct 58.

After second sheath 1b is inserted into bile duct 58, coupling rod 21 is pushed in to advance operating wire 16, thereby projecting basket 17 from the distal end of sheath 1b to spread the basket. Basket 17 is then manipulated to catch calculus 59 in duct 58. If calculus 59 is relatively small, it can be removed by drawing out sheath 1 and the endoscope from the body cavity with the calculus in basket 17.

Figure 7:
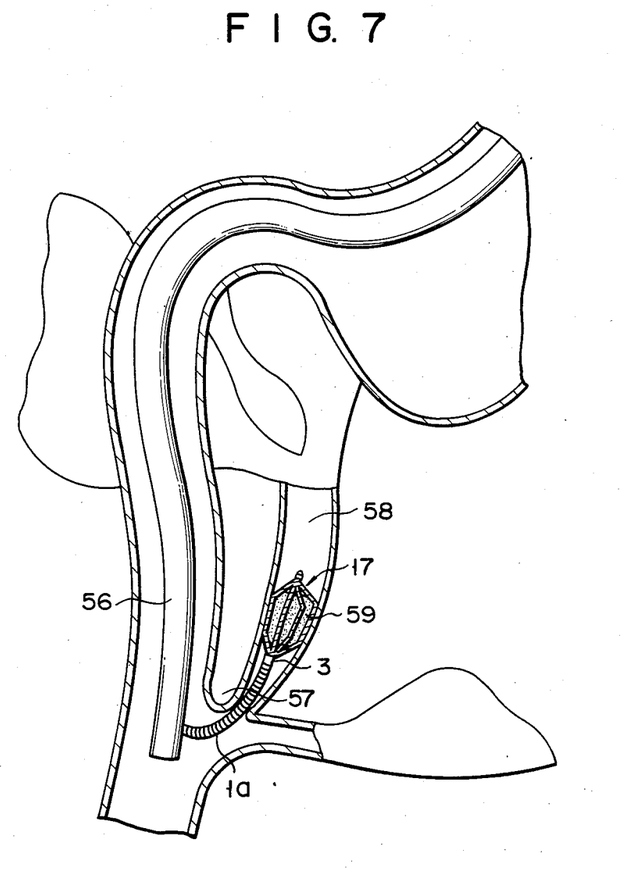
FIG. 7 is a schematic view showing a situation in which the sheath in the state of FIG. 3 is inserted in the body cavity.

If calculus 59 is too bulky to be removed from bile duct 58, first sheath 1a is first advanced along second sheath 1b and inserted into duct 58, as shown in FIG. 7. As a result, the distal end of sheath 1a extends beyond that of sheath 1b. Then, retaining member 4 is screwed into treaded portion 6 of holding cylinder 5 to prevent sheath 1a from sliding, thus locking sheath 1a to the position shown in FIGS. 3 and 7. First sheath 1a is strong enough to stand the calculus crushing operation, but is less flexible than second sheath 1b. Nevertheless, sheath 1a can be inserted into bile duct 58 in a bent configuration maintained securely, guided by sheath 1b. Accordingly, there is no possibility of sheath 1a injuring duodenal papilla 57 or bile duct 58. After sheath 1a is inserted into duct 58, coupling rod 21 is pulled to retreat operating wire 16. As a result, basket 17 is folded by rigid member 3 at the distal end of sheath 1a, so that calculus 59 in basket 17 is broken into pieces by resilient wires 18 which constitute the basket.

Calculus 59 may be crushed by pulling coupling rod 21 by means of operating section 25 connected to mouthpiece 7, instead of manually pulling rod 21. In this case, rod 21 is backed by means of rack structure 31 if knob 46 is rotated. When using section 25, the rotation of handle 46 is slowed down but amplified as it is transmitted to rod 21. Thus, calculus 59 can be crushed gradually with a small force.

According to the calculus crushing apparatus constructed in this manner, the flexible sheath has a dual structure, comprising first sheath 1a having a predetermined strength and second sheath 1b weaker but more flexible than the first one. Sheaths 1a and 1b are movable relative to each other between a position where the distal end of the first sheath extends beyond that of the second one, and a position where the second sheath projects sufficiently beyond the distal end of the first one. If the second sheath is kept projected from the distal end of the first sheath when flexible sheath 1 is inserted into the body cavity, the flexibility of the second sheath serves to facilitate the insertion. In crushing the calculus, the first sheath is moved to the position where its distal end is located beyond that of the second sheath. Thus, with its greater strength, the first sheath can securely accomplish the crushing operation.

Figure 8:
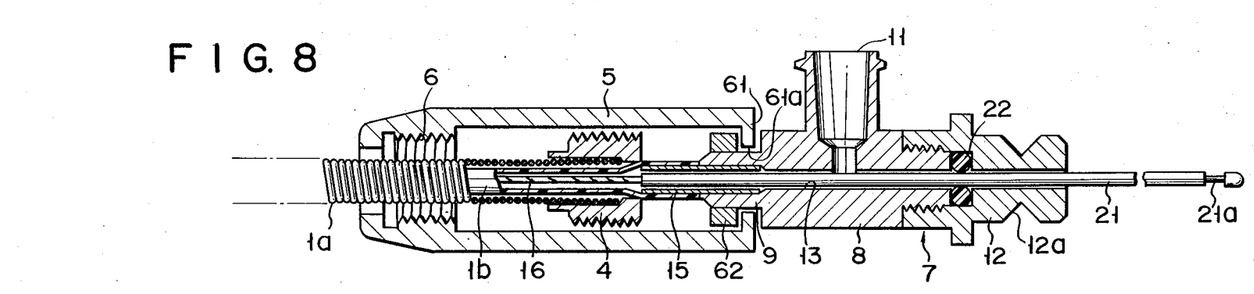
FIG. 8 is a sectional view showing a proximal end portion of a sheath of a crushing apparatus according to a second embodiment of the invention.

FIG. 8 shows a second embodiment of the present invention. This embodiment differs from the first embodiment in the construction of support means for holding cylinder 5. Ring-shaped flange 61 is formed at the proximal end portion of cylinder 5, and boss portion 9 of mouthpiece 7 is inserted through hole 61a which is defined by the inner peripheral surface of flange 61. Ring-shaped stopper 62 is fixed on the outer surface of portion 9, facing flange 61. Thus, holding cylinder 5 is rotatably supported by boss portion 9, and prevented from slipping off portion 9 by stopper 62.

Figure 9:
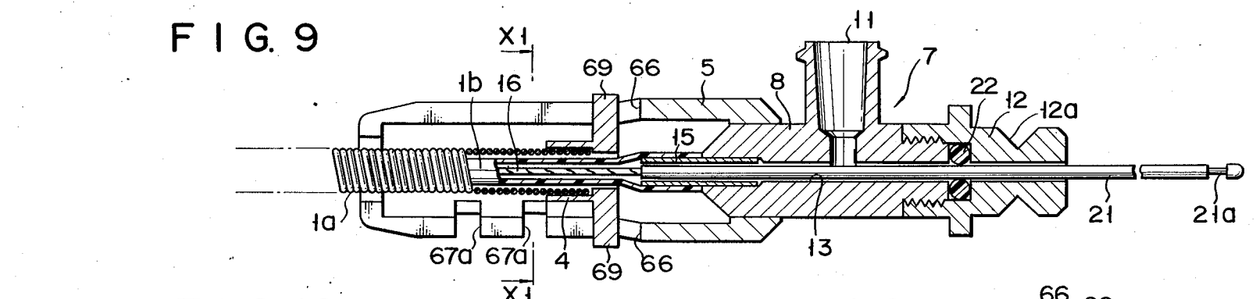
FIG. 9 is a sectional view showing a proximal end portion of a flexible sheath and a mouthpiece.
Figure 10:
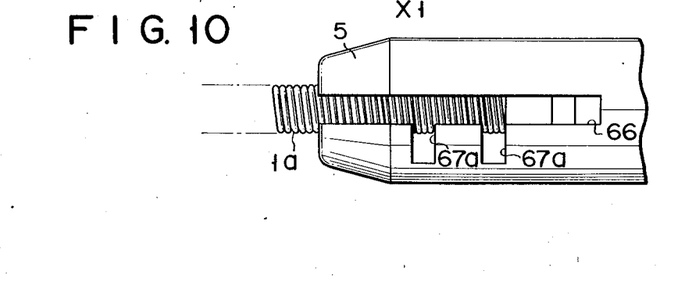
FIG. 10 is a plan view of the proximal end portion of the sheath.
Figure 11:
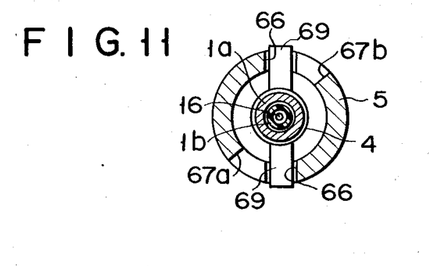
FIG. 11 is a sectional view taken along line XI—XI of FIG. 9.

FIGS. 9, 10 and 11 show a third embodiment of the invention. This embodiment differs from the first embodiment in the construction of retaining means for holding first sheath 1a in position. Retaining member 4 includes, in place of the external threaded portion, a pair of arms 69 which protrude diametrically outward. Arms 69 are spaced at intervals of 180 degrees in the circumferential direction of member 4. The proximal end of holding cylinder 5 is fixed to boss portion 9 of mouthpiece 7. Instead of the internal threaded portion, moreover, a pair of slide grooves 66 are formed on cylinder 5, extending in the axial direction thereof. Grooves 66 are spaced at intervals of 180 degrees in the circumferential direction of cylinder 5, and open to the distal end of cylinder 5. Also, cylinder 5 is formed with a pair of engaging slots 67a extending in the circumferential direction of cylinder 5 and opening into one of grooves 66, and another pair of engaging slots 67b extending in the same direction and opening into the other groove. Slots 67a are spaced along the axis of cylinder 5, while slots 67b are spaced at intervals equal to those between slots 67a along the cylinder axis. Also, slots 67a and 67b are opposed to one another. Arms 69 of retaining member 4 are slidably inserted in their corresponding slide grooves 66, and can engage engaging slots 67a and 67b.

According to this third embodiment, first sheath 1a can be locked in a predetermined position by advancing retaining member 4 to a position where arms 69 face their corresponding engaging slots 67a and 67b, and then rocking member 4 to cause the arms to engage the slots.

Figure 12:
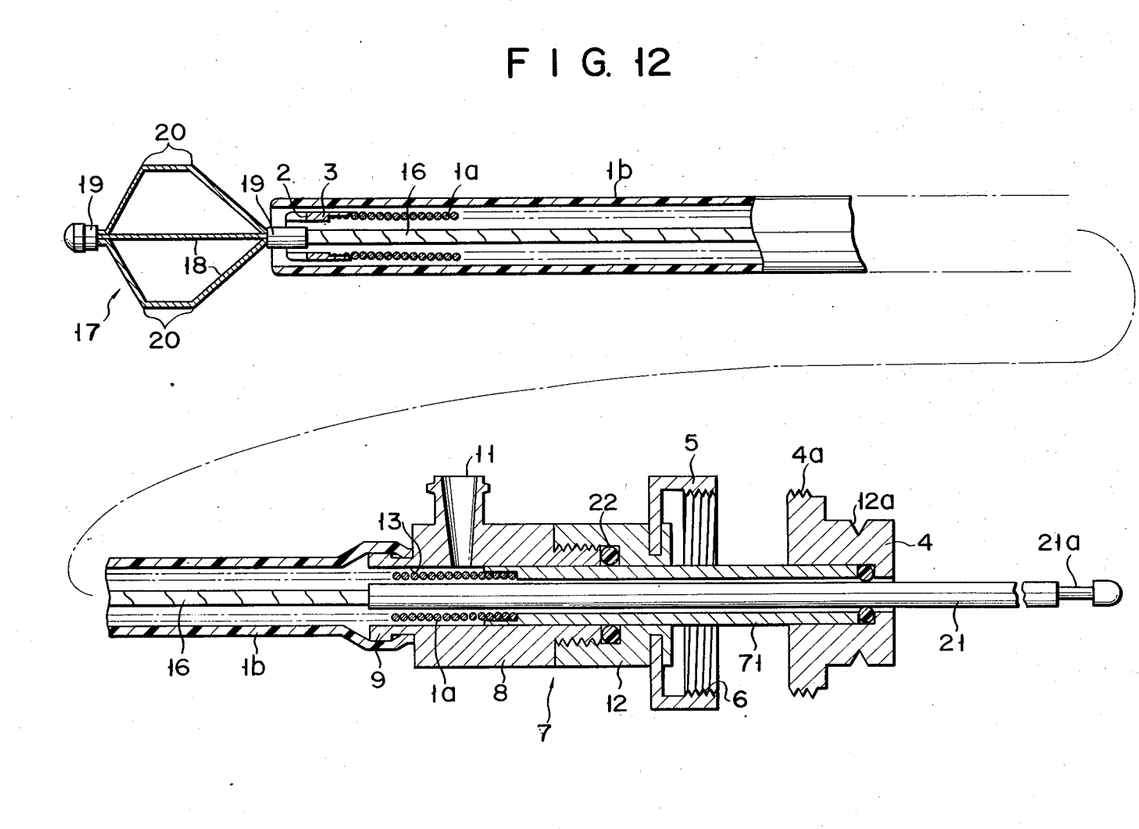
FIG. 12 is a sectional view showing a flexible sheath and a mouthpiece of a crushing apparatus according to a fourth embodiment of the invention.

FIG. 12 shows a fourth embodiment of the present invention. According to this embodiment, first and second sheaths 1a and 1b are positioned in reverse to those of the first embodiment. In FIG. 12, first sheath 1a formed of a close coil is inserted in flexible second sheath 1b formed of synthetic resin or the like. Operating wire 16 is inserted in sheath 1a. The proximal end of sheath 1b is fitted on boss portion 9 of mouthpiece 7. The proximal end of sheath 1a is coupled to guide pipe 71 which is slidably inserted into through hole 13 of mouthpiece 7, projecting rearward therefrom. Coupling rod 21 connected to the proximal end of wire 16 extends through pipe 71. Ring-shaped retaining member 4 having external threaded portion 4a on its outer peripheral surface is fixed on the proximal end portion of pipe 71. Engaging groove 12a for coupling member 4 to the operating section is formed on the outer peripheral surface of member 4. Holding cylinder 5 is rotatably mounted on the rear end portion of mouthpiece 7, and internal threaded portion 6 to engage threaded portion 4a of retaining member 4 is formed on the inner peripheral surface of cylinder 5.

First sheath 1a is moved inside second sheath 1b by advancing or retreating guide pipe 71 and retaining member 4. Sheath 1a can be prevented from sliding by advancing it so that its distal end projects beyond the distal end of sheath 1b, and then screwing member 4 into holding cylinder 5.

In the above description of the second, third and fourth embodiments, like reference numerals have been used to designate like portions as included in the first embodiment. The second to fourth embodiments may provide the same functions or effects of the first embodiment.

What is claimed is:

1. A calculus crushing apparatus for crushing a calculus produced in the body cavity, comprising:
  a flexible sheath adapted to be inserted to be inserted in the body cavity, said sheath including a first sheath having a predetermined mechanical strength sufficient to impart a calculus-crushing force, and a second sheath which is weaker but more flexible than the first sheath, said first and second sheaths being coaxial and movable relative to each other between a first positon where the distal end of the first sheath extends at least to the distal end of the proximity of second sheath, and a second position where the second sheath projects beyond the distal end of the first sheath;

supporting means for supporting the first and second sheaths to be movable relative to each other;

an operating wire slidably inserted in the flexible sheath and adapted to be pushed and pulled from the proximal end side of the sheath;

a collapsible basket for seizing and crushing the calculus, said basket being formed of a plurality of resilient wires connected to the distal end portion of the operating wire, and adapted to be projected from and drawn into the distal end portion of the flexible sheath for expansion and contraction in accordance with the movement of the operating wire; and retaining means for holding the first and second sheaths in the first position in crushing the caluculus seized by the basket.

2. The crushing apparatus according to claim 1, wherein said supporting means includes a mouthpiece attached to the proximal end of the second sheath, and the first sheath is movable relative to the second sheath.

3. The crushing apparatus according to claim 2, wherein said retaining means includes a retaining member fixed to the proximal end of the first sheath, and a holding member attached to the mouthpiece and adapted to engage the retaining member when the first sheath is moved to the first position.

4. The crushing apparatus according to claim 1, wherein said second sheath is passed through the first sheath, and said operating wire is passed through the second sheath.

5. The crushing apparatus according to claim 1, wherein said first sheath is passed through the second sheath, and said operating wire is passed through the first sheath.

6. The crushing apparatus according to claim 1, further comprising operating means connected to the supporting means, for sliding the operating wire.

7. The crushing apparatus according to claim 1, further comprising control means for mainpulating said operating wire to withdraw the basket into said flexible sheath as the first and second sheaths are kept by said retaining means in the first position to subject the basket and its contents to the calculus crushing force imparted by said first sheath.

8. A method for crushing a calculus produced in a body cavity with a flexible sheath having a first sheath formed to impart a calculus crushing force, a second sheath formed to be weaker but more flexible than said first sheath, a wire movable within said flexible sheath, and a collapsible basket attached to the distal end of said wire, and comprising the steps of:

withdrawing said basket into the second sheath by manipulating said wire;

extending said second sheath beyond the distal end of the first sheath to position the flexible sheath into a body cavity;

deploying said basket by operating said wire to position the basket beyond the distal end of said second sheath;

capturing a calculus within said basket, extending said first sheath until its distal end reaches at least to the distal end of said second sheath, and withdrawing said basket into said flexible sheath by forcefully operating said wire to crush the calculus as the basket is collapsed by the force imparted to it by at least said first sheath.

* * * * *